(12) United States Patent
Miyake et al.

(10) Patent No.: US 6,469,080 B2
(45) Date of Patent: Oct. 22, 2002

(54) WATER-ABSORBENT RESIN COMPOSITION

(75) Inventors: Koji Miyake, Okayama (JP); Shinichi Fujino, Himeji (JP); Masatoshi Nakamura, Himeji (JP); Katsuyuki Wada, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/734,190

(22) Filed: Dec. 12, 2000

(65) Prior Publication Data

US 2001/0053807 A1 Dec. 20, 2001

(30) Foreign Application Priority Data

Dec. 15, 1999 (JP) .............................. 11-356309

(51) Int. Cl.⁷ .............................. C08K 5/09; C08K 5/04
(52) U.S. Cl. ...................... 524/239; 524/321; 524/395; 524/556; 524/560; 523/102
(58) Field of Search ................. 524/239, 321, 524/395, 556, 560; 523/102

(56) References Cited

U.S. PATENT DOCUMENTS

| | | | |
|---|---|---|---|
| 5,078,992 A | 1/1992 | Takahashi et al. | ......... 424/76.3 |
| 5,369,148 A | 11/1994 | Takahashi et al. | .......... 523/315 |

FOREIGN PATENT DOCUMENTS

| | | |
|---|---|---|
| EP | 0811390 | 12/1997 |
| EP | 0940148 | 9/1999 |
| EP | 0942014 | 9/1999 |
| JP | 09085082 | 3/1997 |
| JP | 11246674 | 9/1999 |

OTHER PUBLICATIONS

"TR–6 Bioassays of Nitrilotriacetic Acid (NTA) and Nitrilotriacetic Acid, Trisodium Salt, Monohydrate (Na3–NTA–H20) for Possible Carcinogenicity (CAS No. 139–13–9) (NTA) (CAS No. 18662–53–8) (Na3–NTA–H2O)", Techn. Report NTIS, 'Online! Jan. 1977, XP002162685.

"Ethylenediaminetetraacetic Acid and Realted Chelating Agents"; Hart et al.; Ullmann's Encyclopedia of Industrial Chemistry; 5$^{th}$ Ed. vol. A 10; 1987; pp. 95–100; XP002162686.

*Primary Examiner*—Kriellion A. Sanders
(74) *Attorney, Agent, or Firm*—Roylance, Abrams, Berdo & Goodman, L.L.P.

(57) ABSTRACT

The present invention provides a water-absorbent resin composition which contains an aminoacetic chelating agent and is excellent in the urine resistance, wherein the water-absorbent resin composition is excellent further in the light resistance and becomes little colored and might have deodorizability. A water-absorbent resin composition, which comprises a water-absorbent resin and an aminoacetic chelating agent, wherein the mixing ratio of the aminoacetic chelating agent in the water-absorbent resin composition is not less than 10 ppm of the water-absorbent resin, and wherein the total content of nitrilotriacetic acid and its salt in the water-absorbent resin composition is not more than 1 ppm of the water-absorbent resin composition.

19 Claims, 1 Drawing Sheet

WATER-ABSORBENT RESIN COMPOSITION

BACKGROUND OF THE INVENTION

A. Technical Field

The present invention relates to a water-absorbent resin composition. Specifically, the invention relates to a water-absorbent resin composition wherein the water-absorbent resin composition is excellent in the urine resistance and the light resistance, and becomes little colored. Furthermore, the invention relates to a water-absorbent resin composition which is excellent also in the deodorizability.

B. Background Art

In recent years, water-absorbent resins are widely used as components of sanitary materials, such as disposable diapers, sanitary napkins and incontinent pads, for the purpose of causing the water-absorbent resins to absorb body liquids such as urine and menstrual blood.

As to the above water-absorbent resins, the following are known as their examples: partially-neutralized and crosslinked poly(acrylic acids); hydrolyzed graft polymers of starch-acrylonitrile; neutralized graft polymers of starch-acrylic acid; saponified copolymers of vinyl acetate-acrylic acid ester; crosslinked polymers of carboxymethyl cellulose; hydrolyzed copolymers of acrylonitrile or acrylamide, or crosslinked polymers of these hydrolyzed copolymers; crosslinked polymers of cationic monomers; crosslinked copolymers of isobutylene-maleic acid; and crosslinked copolymers of 2-acrylamido-2-methylpropanesulfonic acid-acrylic acid.

There is a problem which has hitherto been pointed out. The problem is that: in the case where the water-absorbent resin is used as an absorbent structure for disposable diapers, the water-absorbent resin deteriorates with the passage of time, so that its liquid permeability or gel strength becomes low, resulting in urine leakage from the disposable diapers. Such a deterioration of the water-absorbent resin due to urine is considered to be caused by a very small amount of metal ion and by L-ascorbic acid which is contained in urine. Thus, there is a proposed art in which a so-called chelating agent is added to the water-absorbent resin to scavenge the metal ion, thereby enhancing the urine resistance of the water-absorbent resin. Known examples of such a chelating agent include aminoacetic cheating agents such as sodium diethylenetriaminepentaacetate and sodium triethylenetetraminehexaacetate (JP-A-246674/1999, EP 940148A).

From structures of the aminoacetic chelating agents, it is expected that the aminoacetic chelating agents are able to enhance not only the urine resistance, but also the light resistance of the water-absorbent resin. However, prior arts enhance the urine resistance only and, as to the light resistance, provide the same results as those from no addition of the aminoacetic chelating agents.

On the other hand, the water-absorbent resin is desired to become little colored with the passage of time from a point of view that the water-absorbent resin is mainly used for sanitary materials (EP 942014). In addition, it is also desired to reduce the offensive odor which is emitted, for example, when the water-absorbent resin absorbs urine (U.S. Pat. No. 5,078,992, JP-A-085082/1997).

SUMMARY OF THE INVENTION

A. Objects of the Invention

A first object of the present invention is to provide a water-absorbent resin composition which contains an aminoacetic chelating agent and is excellent in the urine resistance, wherein the water-absorbent resin composition is excellent further in the light resistance. A second object of the present invention is to provide a water-absorbent resin composition which becomes little colored, and further, little smells bad when used.

B. Disclosure of the Invention

As a result of the present inventors' diligent study to solve the above problems, it has been found that a cause of the non-enhancement of the light resistance in spite of the addition of the aminoacetic chelating agent in prior arts is nitrilotriacetic acid and/or its salt (hereinafter, for simplification, both might be generically referred to as "nitrilotriacetic acid (salt)") which are contained as impurities in a concentration of not lower than several weight percent (usually, about 5 to about 15 weight %) in the aminoacetic chelating agent. The nitrilotriacetic acid (salt) is also a substance which gives anxiety that it might be carcinogenic (rank 2B in IARC). Therefore, its content must be reduced as much as possible also from a viewpoint of safety, considering that the water-absorbent resin composition is used for things contacting human bodies such as disposable diapers.

The aminoacetic chelating agent is generally produced by a process including the steps of causing ammonia to react with ethylene dichloride or aziridine to form a product such as diethylenetriamine or triethylenetetramine, and then causing this product to react with chloroacetic acid and an alkali agent such as sodium hydroxide. However, it is considered that unreacted ammonia remains in the above product such as diethylenetriamine or triethylenetetramine, and therefore reacts with chloroacetic acid to form the nitrilotriacetic acid (salt) as impurities.

From the results verified by the present inventors' experiments, it has been found that the total content of the nitrilotriacetic acid (salt) in the water-absorbent resin composition needs to be reduced to not more than 1 ppm, preferably not more than 0.5 ppm, more preferably not more than 0.1 ppm (herein, unless otherwise noted, "ppm" is by weight), of the water-absorbent resin composition from a point of view of enhancing the light resistance, and further that if the total content of the nitrilotriacetic acid (salt) in the water-absorbent resin composition is reduced to such a degree, the coloring of the water-absorbent resin composition is also little. However, if an attempt is made to reduce the total content of the nitrilotriacetic acid (salt) in the water-absorbent resin composition by simply reducing the mixing ratio of the aminoacetic chelating agent, the light resistance may be enhanced, but on the other hand the urine resistance is extremely deteriorated, that is to say, it becomes difficult to keep or enhance the urine resistance by adding the chelating agent. From the results verified by the present inventors' experiments, it has been found that the mixing ratio of the aminoacetic chelating agent in the water-absorbent resin composition needs to be restricted to not less than 10 ppm, preferably not less than 20 ppm, of the water-absorbent resin from a point of view of keeping or enhancing the urine resistance.

From the above, it has been found that a water-absorbent resin composition which is excellent not only in the urine resistance, but also in the light resistance, and further, becomes little colored is obtained if the mixing ratio of the aminoacetic chelating agent in the water-absorbent resin composition is restricted to not less than 10 ppm of the water-absorbent resin and further if the total content of the nitrilotriacetic acid (salt) in the water-absorbent resin composition is restricted to not more than 1 ppm, preferably not more than 0.5 ppm, more preferably not more than 0.1 ppm, of the water-absorbent resin composition. Thus, the present invention has been completed.

The present inventors further studied diligently about a process for reducing the total content of the nitrilotriacetic acid (salt) in the aminoacetic chelating agent in order to facilitate the above execution, namely, the execution of the restrictions of the mixing ratio of the aminoacetic chelating agent in the water-absorbent resin composition to not less than 10 ppm of the water-absorbent resin and further the total content of the nitrilotriacetic acid (salt) in the water-absorbent resin composition to not more than 1 ppm of the water-absorbent resin composition. As a result, it has been found that when both the aminoacetic chelating agent and the nitrilotriacetic acid are in salt form (—COOX (X: e.g. alkaline metal)), both have high water solubility and are therefore difficult to separate from each other, but that when both are in acid form (—COOH), the aminoacetic chelating agent has low water solubility, while the nitrilotriacetic acid has high water solubility. Thus, the inventors have completed the present invention by finding that an aminoacetic chelating agent having an extremely reduced total content of the nitrilotriacetic acid (salt) for the water-absorbent resin is obtained if the above difference in water solubility is utilized to carry out a process including the steps of: adjusting pH of an aqueous solution of an aminoacetic chelating agent containing the nitrilotriacetic acid (salt) into the range of 1 to 3 to deposit a precipitate (the acid form of aminoacetic chelating agent); recovering the deposited precipitate by its separation; and washing and then drying the recovered precipitate, if necessary.

Thus, to solve the aforementioned problems, the present invention provides the following:

(1) A water-absorbent resin composition, which comprises a water-absorbent resin and an aminoacetic chelating agent, wherein the mixing ratio of the aminoacetic chelating agent in the water-absorbent resin composition is not less than 10 ppm of the water-absorbent resin, and wherein the total content of nitrilotriacetic acid and its salt in the water-absorbent resin composition is not more than 1 ppm of the water-absorbent resin composition.

(2) A water-absorbent resin composition, which comprises a water-absorbent resin and an aminoacetic chelating agent, wherein the total content of nitrilotriacetic acid and its salt relative to the aminoacetic chelating agent in the water-absorbent resin composition is not more than 1,000 ppm.

(3) A water-absorbent resin composition according to (1) or (2) above, which further comprises a water-soluble deodorant.

(4) A water-absorbent resin composition according to any one of (1) to (3) above, which exhibits an absorption capacity of not less than 30 g/g without load, an eluted deteriorated extractable content of not more than 20 weight %, an absorption capacity of not less than 28 g/g under a load of 1.9 kPa, and a yellowness index of not more than 26.

(5) A water-absorbent resin composition, which comprises a water-absorbent resin and a water-soluble deodorant and exhibits an absorption capacity of not less than 30 g/g without load, an eluted deteriorated extractable content of not more than 20 weight %, an absorption capacity of not less than 28 g/g under a load of 1.9 kPa, and an offensive-odor reduction ratio of not less than 40%.

These and other objects and the advantages of the present invention will be more fully apparent from the following detailed disclosure.

DETAILED DESCRIPTION OF THE INVENTION

Figure 1:
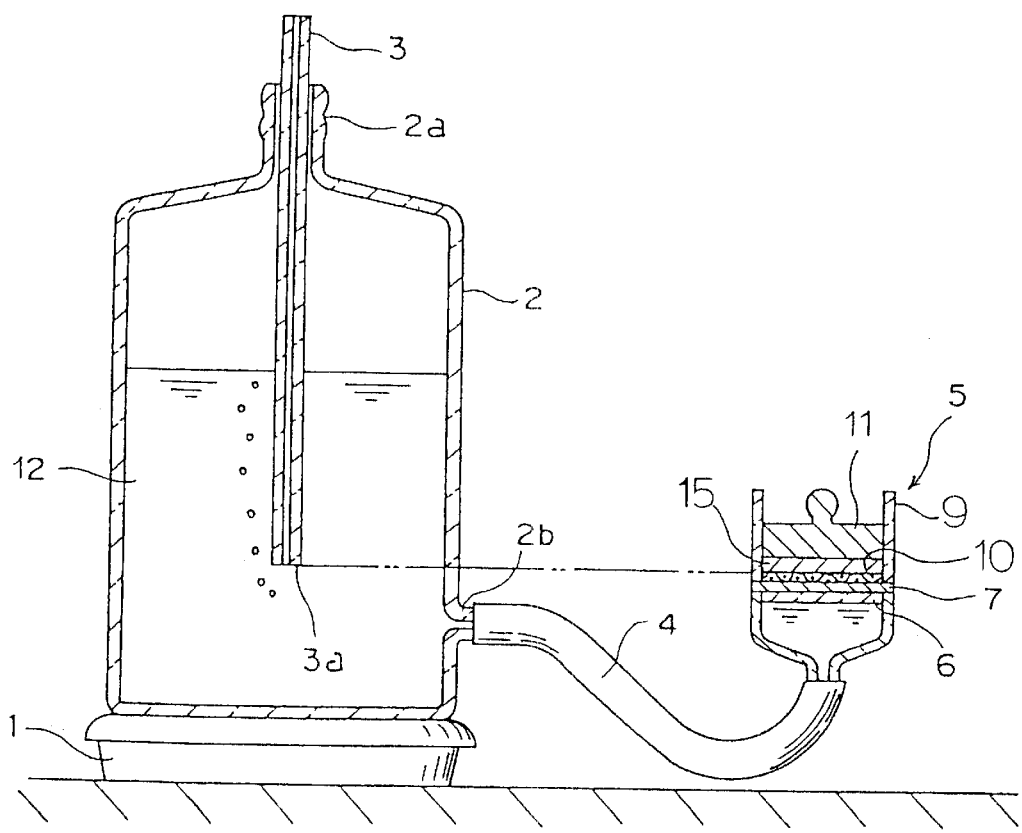
FIG. 1 illustrates a measurement apparatus for the absorption capacity under a load.

The water-absorbent resin composition, according to the present invention, comprises a water-absorbent resin and an aminoacetic chelating agent, wherein the mixing ratio of the aminoacetic chelating agent in the water-absorbent resin composition is not less than 10 ppm of the water-absorbent resin, and wherein the total content of the nitrilotriacetic acid (salt) in the water-absorbent resin composition is not more than 1 ppm of the water-absorbent resin composition.

Such restrictions can easily be achieved, for example, in a way that an aminoacetic chelating agent in which the total content of the nitrilotriacetic acid (salt) is not more than 1,000 ppm of the aminoacetic chelating agent is used as the aminoacetic chelating agent. However, there is no limitation to this way.

The aminoacetic chelating agent with such an extremely low total content of the nitrilotriacetic acid (salt) is not limited, but is, for example, obtainable by a process including the steps of: adjusting pH of an aqueous solution of a commercially available aminoacetic chelating agent into the range of 1 to 3 to deposit a precipitate wherein the aminoacetic chelating agent contains the nitrilotriacetic acid (salt) as impurities; and then recovering the deposited precipitate by its separation.

The method for adjusting pH of the aqueous solution of the aminoacetic chelating agent containing the nitrilotriacetic acid (salt) into the range of 1 to 3 is not especially limited, but may be carried out by adding an acid such as sulfuric acid, nitric acid, or hydrochloric acid to the above aqueous solution. The pH of the aqueous solution is preferably adjusted into the range of 1.5 to 2.5, more preferably 1.8 to 2.0. It is simple that the recovery of the precipitate by its separation is carried out by filtration. The washing of the precipitate recovered by its separation is preferably carried out with pure water, and the drying of the washed precipitate is preferably carried out in the range of 50 to 200° C.

The total content of the nitrilotriacetic acid (salt) in the aminoacetic chelating agent can be reduced to not more than 1,000 ppm, preferably not more than 500 ppm, more preferably not more than 200 ppm, still more preferably not more than 100 ppm, of the aminoacetic chelating agent by the above process.

If the aminoacetic chelating agent having an extremely reduced total content of the nitrilotriacetic acid (salt), obtained by the above process, is added to the water-absorbent resin or its raw material, the total content of the nitrilotriacetic acid (salt) in the water-absorbent resin composition can be rendered very low, specifically, preferably not more than 1 ppm, more preferably not more than 0.5 ppm, still more preferably not more than 0.1 ppm, yet still more preferably not more than 0.01 ppm, of the water-absorbent resin composition.

When the aminoacetic chelating agent is added to the water-absorbent resin or its raw material is not especially limited, but, for example, the aminoacetic chelating agent can be added (1) to a monomer, or (2) to the resulting gel on the way of polymerization or after polymerization, or (3) during surface-crosslinking treatment, or (4) after surface-crosslinking treatment, or (5) in the recovery step of recovering fine particles of the water-absorbent resin. Particularly preferable is the addition during or after surface-crosslinking treatment.

The aminoacetic chelating agent can be added to the water-absorbent resin or its raw material after being dissolved or dispersed into water or an organic solvent (e.g. methanol, ethanol, isopropanol, acetone), but is preferably added after being dissolved into an alkali solution because, as is mentioned above, the acid type has low water solubility. The concentration of the aminoacetic chelating agent solution is preferably in the range of 0.1 to 40 weight %, more preferably 1 to 40 weight %.

The aminoacetic chelating agent can be added so that its amount will be in the range of 1 ppm to 10 weight %, preferably 5 to 1,000 ppm, more preferably 10 to 800 ppm, of the water-absorbent resin. In the case where the amount of the aminoacetic chelating agent used is too small, the urine resistance enhancement effect is not seen. In the case where the amount of the aminoacetic chelating agent used is too large, no effect rewarding this amount is obtained.

The amount of the aminoacetic chelating agent relative to the water-absorbent resin in the resultant water-absorbent resin composition depends on how to add the aminoacetic chelating agent to the water-absorbent resin, but is substantially the same as the above amount of the aminoacetic chelating agent as added to the water-absorbent resin.

Usable examples of the aminoacetic chelating agent include ethylenediaminetetraacetic acid, hydroxyethylethylenediaminetriacetic acid, diethylenetriaminepentaacetic acid, triethylenetetraminehexaacetic acid, cyclohexanediaminotetraacetic acid, and their alkaline metal salts, ammonium salts, and amine salts. Particularly preferable are diethylenetriaminepentaacetic acid, triethylenetetraminehexaacetic acid, and their alkaline metal salts.

The water-absorbent resin, usable for the water-absorbent resin composition according to the present invention, absorbs a large quantity of water in water to thereby form a hydrogel, and examples thereof include those which have a carboxyl group, specifically, such as: partially-neutralized and crosslinked poly(acrylic acids); hydrolyzed graft polymers of starch-acrylonitrile; neutralized graft polymers of starch-acrylic acid; saponified copolymers of vinyl acetate-acrylic acid ester; crosslinked polymers of carboxymethyl cellulose; hydrolyzed copolymers of acrylonitrile or acrylamide, or crosslinked polymers of these hydrolyzed copolymers; crosslinked polymers of cationic monomers; crosslinked copolymers of isobutylene-maleic acid; and crosslinked copolymers of 2-acrylamido-2-methylpropanesulfonic acid-acrylic acid. The most preferable of these are the partially-neutralized and crosslinked poly(acrylic acids).

The partially-neutralized and crosslinked poly(acrylic acid) can be obtained by a process including the step of polymerizing hydrophilic monomers including a major proportion of acrylic acid and/or its salt. The ratio of monomers other than acrylic acid and/or its salt is preferably not larger than 30 mol % of the monomer components. As to the neutralization ratio, preferably 50 to 95 mol %, more preferably 60 to 90 mol %, of acid groups are neutralized. Examples of salts include alkaline metal salts, ammonium salts, and amine salts. Aqueous solution polymerization or reversed-phase suspension polymerization is preferably carried out as the polymerization method.

To crosslink a partially neutralized poly(acrylic acid) resultant from the polymerization, a self-crosslinking type of partially neutralized poly(acrylic acid) needing no crosslinking agent is usable, but it is preferable to carry out a copolymerization or reaction of the partially neutralized poly(acrylic acid) with an internal-crosslinking agent having at least two polymerizable unsaturated groups or at least two reactive groups per molecule.

Specific examples of the internal-crosslinking agent include: N,N'-methylenebis(meth)acrylamide, (poly)ethylene glycol di(meth)acrylate, (poly)propylene glycol di(meth)acrylate, trimethylolpropane tri(meth)acrylate, glycerol tri(meth)acrylate, glycerol acrylate methacrylate, ethylene-oxide-modified trimethylolpropane tri(meth)acrylate, pentaerythritol tetra(meth)acrylate, dipentaerythritol hexa(meth)acrylate, triallyl cyanurate, triallyl isocyanurate, triallyl phosphate, triallylamine, poly(meth)allyloxyalkanes, (poly)ethylene glycol diglycidyl ether, glycerol diglycidyl ether, ethylene glycol, polyethylene glycol, propylene glycol, glycerol, pentaerythritol, ethylenediamine, ethylene carbonate, propylene carbonate, polyethylenimine, and glycidyl (meth)acrylate. These internal-crosslinking agents may be used either alone respectively or in combinations with each other.

The amount of the internal-crosslinking agent as used is preferably in the range of 0.005 to 3 mol %, more preferably 0.01 to 1.5 mol %, of the aforementioned monomer components. Too small an amount of internal-crosslinking agent tends to result in low liquid permeability and absorption rate. On the other hand, too large an amount of internal-crosslinking agent tends to result in low absorption capacity.

When the polymer resultant from the above polymerization is a hydrogel, this hydrogel is desired to be finely particulated into a predetermined particle diameter in order to dry the hydrogel thereafter. The fine particulation of the hydrogel, for example, can be carried out during the polymerization by doing the polymerization under stirred conditions with such as twin-arm kneaders, or can be carried out by extruding the gel from dies with such as meat choppers after the polymerization. In addition, the fine particulation can also be carried out with such as cutting mills. The particle diameter of the finely particulated gel can fitly be set according to such as ability of driers, but is generally preferably in the range of 0.1 to 10 mm. In the case where the particulated gel is finer than 0.1 mm, the physical properties of the resultant water-absorbent resin might be inferior. In the case where the particulated gel is coarser than 10 mm, the gel might be difficult to dry.

In the fine particulation step, a coarse gel with a particle diameter larger than 10 mm and a fine gel with a particle diameter smaller than 0.1 mm might form. These polymers can be separated and then added to such as an aqueous monomer solution or a polymer gel.

The gel as finely particulated in the above fine particulation step is dried in the drying step. Examples of usable means for drying include hot-air driers, gas current driers, fluidized-bed driers, drum driers, microwaves, and far infrared rays. The drying temperature is usually not lower than 120° C., preferably in the range of 150 to 250° C., more preferably in the range of 160 to 220° C. The resultant dried product is pulverized (if necessary) and then classified with a sieve of the predetermined size, with the result that a water-absorbent resin powder having an average particle diameter of about 10 to about 1,000 $\mu$m, preferably about 100 to about 700 $\mu$m, more preferably about 300 to about 500 $\mu$m, and containing fine particles smaller than 106 $\mu$m in a ratio of not more than 5 weight %, preferably not more than 3 weight %, more preferably not more than 1 weight %, can be obtained.

Fine particles, removed by the classification, of the water-absorbent resin can be recovered and then recycled and then added in any of the steps for producing the water-absorbent resin.

The particle diameter of the recovered water-absorbent resin (fine particles) is not especially limited, but is generally not larger than 300 μm, preferably not larger than 225 μm, more preferably not larger than 150 μm.

The recovered water-absorbent resin may be either what it is before or after being treated by surface crosslinking, and either water-absorbent resin is usable.

To recycle the recovered fine particles, water is added thereto to granulate them. The amount of water as added is preferably in the range of 0.1 to 2,000 weight parts, more preferably 10 to 900 weight parts, per 100 weight parts of the water-absorbent resin. In the case where the amount of water as added is smaller than the above range, recycling is difficult. In addition, in the case where the amount of water as added is larger than the above range, the recycled water-absorbent resin easily deteriorates.

In the case where the aminoacetic chelating agent is added in the step of recovering the fine particles, an aqueous solution of the chelating agent may be added to the fine particles, or the chelating agent may be added to a mixture of water and the fine particles. In addition, it is also permissible that a dry blend of the chelating agent and the fine particles is mixed with water.

The crosslinking treatment of the vicinity of surfaces of the water-absorbent resin powder can more enhance the water absorption properties, particularly, absorption capacity under a load, of the water-absorbent resin. Examples of the surface-crosslinking agent include those which are disclosed in JP-A-180233/1983, JP-A-016903/1986, JP-A-189103/1984, JP-A-117393/1977, JP-A-136588/1976, JP-A-257235/1986, JP-A-007745/1987, JP-A-211305/1986, JP-A-252212/1986, JP-A-264006/1986, German Patent No. 4020780, WO 99/42494, WO 99/43720, WO 00/31153, and JP-A-197818/2000. Specifically, there is no limitation in the surface-crosslinking agent if it has at least two functional groups reactable with surface functional groups of the water-absorbent resin. Examples of the surface-crosslinking agent include: polyhydric alcohol compounds such as ethylene glycol, diethylene glycol, propylene glycol, triethylene glycol, tetraethylene glycol, polyethylene glycol, 1,3-propanediol, dipropylene glycol, 2,2,4-trimethyl-1,3-pentanediol, polypropylene glycol, glycerol, polyglycerol, glycerophosphoric acid, 2-butene-1,4-diol, 1,3-butanediol, 1,4-butanediol, 1,5-pentanediol, 1,6-hexanediol, 1,2-cyclohexanedimethanol, 1,2-cyclohexanol, trimethylolpropane, diethanolamine, triethanolamine, polyoxypropylene, oxyethylene-oxypropylene block copolymers, pentaerythritol and sorbitol; polyepoxy compounds such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether and glycidol; polyamine compounds, such as ethylenediamine, diethylenetriamine, triethylenetetramine, tetraethylenepentamine, pentaethylenehexamine and polyethylenimine, and their inorganic or organic salts (for example, azetidinium salts); polyisocyanate compounds such as 2,4-tolylene diisocyanate and hexamethylene diisocyanate; polyoxazoline compounds such as 1,2-ethylenebisoxazoline, polyisopropenyloxazoline, and copolymers thereof; alkylene carbonate compounds such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one and 1,3-dioxopan-2-one; haloepoxy compounds, such as epichlorohydrin, epibromohydrin and α-methylepichlorohydrin, and their polyamine adducts (for example, Kymene (registered trademark) made by Hercules); silane coupling agents such as γ-glycidoxypropyltrimethoxysilane and γ-aminopropyltriethoxysilane; and polyvalent metallic compounds such as hydroxides and chlorides of zinc, calcium, magnesium, aluminum, iron and zirconium. Preferable among them are the polyhydric alcohol compounds, the polyepoxy compounds, the polyamine compounds or their salts, and the alkylene carbonate compounds. These surface-crosslinking agents may be used either alone respectively or in combinations with each other.

The amount of the surface-crosslinking agent, as used, is preferably in the range of 0.01 to 10 weight parts, more preferably 0.1 to 5 weight parts, per 100 weight parts of the water-absorbent resin. In the case where the amount of the surface-crosslinking agent as added is smaller than 0.01 weight parts, the surface-crosslinking is insufficient. In the case where the surface-crosslinking agent is used in an amount larger than 10 weight parts, the resultant absorption capacity might be extremely low.

After mixing the water-absorbent resin and the surface-crosslinking agent together, the resultant mixture is subjected to a heating treatment, if necessary. Conventional driers or heating-furnaces can be used for the heating treatment, and examples thereof include channel type stirring driers, rotary driers, disk driers, fluidized-bed driers, gas current driers, and infrared driers. When the heating treatment is carried out, the heating treatment temperature is preferably in the range of 40 to 250° C., more preferably 90 to 230° C., still more preferably 120 to 220° C. In the case where the heating treatment temperature is lower than 40° C., so long a time is needed for the heating treatment that the productivity is lowered. On the other hand, in the case where the heating treatment temperature is higher than 250° C., there is a danger that the water-absorbent resin might be thermally deteriorated according to the sort of the water-absorbent resin as used. The heating treatment period of time is usually in the range of preferably 1 to 120 minutes, more preferably 10 to 60 minutes.

In the case where the aminoacetic chelating agent is added in the surface-crosslinking treatment step, the water-absorbent resin is mixed with the surface-crosslinking agent and the aminoacetic chelating agent and, if necessary, the resultant mixture is subjected to the heating treatment. In the above mixing step, water is preferably used. The amount of water is preferably in the range of 0.5 to 10 weight parts, more preferably 0.5 to 3 weight parts, per 100 weight parts of the water-absorbent resin. In the case where the amount of water as added is smaller than the above range, it is difficult to fix the aminoacetic chelating agent onto surfaces of water-absorbent resin particles. In addition, in the case where the amount of water as added is larger than the above range, the absorption capacity of the water-absorbent resin might be lowered. Conditions for the heating treatment are the same as those in the case where no aminoacetic chelating agent is added.

In the case where the aminoacetic chelating agent is added after the surface-crosslinking treatment step, it is preferable that the aminoacetic chelating agent and water are added to the surface-crosslinking-treated water-absorbent resin by such as spraying to thereby bind particles of the water-absorbent resin to each other with water as a binder, thus granulating them together. Thereby the aminoacetic chelating agent can be fixed onto surfaces of the water-absorbent resin. The deterioration of the water-absorbent resin due to urine occurs from surfaces of the resin, therefore the urine resistance can be enhanced by placing the aminoacetic chelating agent in the vicinity of surfaces of the water-absorbent resin. The amount of water as used then is preferably in the range of 0.1 to 20 weight parts, more preferably 0.1 to 10 weight parts, still more preferably 0.5 to 4 weight parts, per 100 weight parts of the water-absorbent resin. In the case where the amount of water as added is smaller than the above range, it is difficult to granulate the water-absorbent resin particles, and further, it is difficult to fix the aminoacetic chelating agent onto surfaces of the water-absorbent resin particles. In addition, in the case where the amount of water as added is larger than the above range, the water-absorbent resin swells up to its inner portion to form a gel, therefore the aimed granulated product might not be obtained and further the surface-crosslinked layers of the water-absorbent resin particle surfaces might be broken.

The water-absorbent resin composition, according to the present invention, can further comprise a water-soluble deodorant in order for the water-absorbent resin composition to exhibit the deodorizability. Incidentally, the reason why a water-soluble one is used as the deodorant is that the water-soluble deodorant gives excellent deodorizability to the water-absorbent resin composition without deteriorating the absorption performance of the water-absorbent resin composition. Herein, the water-soluble deodorant is such that not less than 0.1 g, preferably not less than 1 g, more preferably not less than 10 g, of the deodorant is soluble in 100 g of deionized water at room temperature. As to such a deodorant, various conventional ones such as extractates from leaves of Theaceae plants are usable. Example of the Theaceae plants include camellia, tea plant, sasanqua camellia, sakaki plant, and scarlet sakaki plant, and deodorizable components are extractable from their leaves with organic solvents, such as alcohols and ketones, or water, or their mixed solvents. The extracted components include flavonol, flavanols, organic polymers, or tannin. The mixing ratio of the deodorant is preferably in the range of 0.0001 weight % (1 ppm) to 10 weight % of the water-absorbent resin. In the case where the mixing ratio of the deodorant is smaller than the above range, the deodorizing effect is not exhibited. In addition, in the case where the mixing ratio of the deodorant is larger than the above range, no effect rewarding an increase of costs is obtained. The deodorant is mixed into the water-absorbent resin composition, for example, by: 1) dissolving the deodorant into water or organic solvents such as alcohols, and then spraying the resultant solution to the water-absorbent resin (or its composition); or 2) adding the deodorant along with the water-absorbent resin into solvents which do not swell the water-absorbent resin (or its composition), and then stirring them together to make a mixture, and then removing the solvents from the mixture; or 3) powdering or granulating the deodorant, and then mixing the resultant powder or granules with the water-absorbent resin (or its composition). Preferably, the deodorant is added simultaneously with the above granulation or with the addition of the chelating agent.

Examples of deodorants other than the above extractates from leaves of the Theaceae plants include: organic acids such as acetic acid, citric acid, and lactic acid; iron chlorophyrin sodium; copper chlorophyrin sodium; cyclodextrin; and flavonoid compounds. The mixing ratio of these other deodorants is preferably in the range of about 0.0001 weight % (1 ppm) to about 10 weight % of the water-absorbent resin.

The above-mentioned water-absorbent resin composition, according to the present invention, has the following properties:

(1) The absorption capacity without load is not less than 30 g/g, preferably not less than 34 g/g, more preferably not less than 40 g/g; the eluted deteriorated extractable content is not more than 20 weight %, preferably not more than 18 weight %, more preferably not more than 16 weight %; the absorption capacity under a load of 1.9 kPa is not less than 28 g/g, preferably not less than 30 g/g, more preferably not less than 32 g/g; and the yellowness index is not more than 26, preferably not more than 24, more preferably not more than 22.

(2) The absorption capacity without load is not less than 30 g/g, preferably not less than 34 g/g, more preferably not less than 40 g/g; the eluted deteriorated extractable content is not more than 20 weight %, preferably not more than 18 weight %, more preferably not more than 16 weight %; the absorption capacity under a load of 1.9 kPa is not less than 28 g/g, preferably not less than 30 g/g, more preferably not less than 32 g/g; and the offensive-odor reduction ratio is not less than 40%, preferably not less than 45%, more preferably not less than 50%.

In the case where a water-absorbent resin composition exhibiting an absorption capacity less than 30 g/g without load is used for absorbent articles, the absorption quantity of the absorbent articles is small, and the leakage easily occurs.

In the case where a water-absorbent resin composition exhibiting an eluted deteriorated extractable content more than 20 weight % is used for absorbent articles, a slimy feeling is much given in long-time use.

In the case where a water-absorbent resin composition exhibiting an absorption capacity less than 28 g/g under a load of 1.9 kPa is used for absorbent articles, the absorption quantity of the absorbent articles is small, and the leakage easily occurs.

In the case where a water-absorbent resin composition exhibiting a yellowness index more than 26 is used for absorbent articles such as disposable diapers and napkins, the absorbent articles easily become colored during their preservation, so that the water-absorbent resin composition is seen through surfaces of the absorbent articles. If the yellowness index is not more than 26, the preservation durability is good, and further, the water-absorbent resin composition cannot be seen through surfaces of the absorbent articles, with the result that consumers' complaints decrease.

In the case where a water-absorbent resin composition exhibiting an offensive-odor reduction ratio less than 40% is used for diapers, the deodorizing effect is low or is not exhibited at all. However, if a water-absorbent resin composition exhibiting an offensive-odor reduction ratio of not less than 40% is used, the deodorizing effect is seen.

As to the water-absorbent resin composition according to the present invention, it is permissible to afford new functions to the water-absorbent resin composition by adding thereto materials such as perfumes, chemicals, plant growth assistants, fungicides, foaming agents, pigments, dyes, and fertilizers.

The water-absorbent resin composition according to the present invention comprises particles having various shapes such as irregular pulverized shapes, spherical shapes, bar shapes, and granular shapes, and has a weight-average particle diameter in the range of preferably 100 to 600 $\mu$m, more preferably 200 to 500 $\mu$m. In addition, the ratio of the water-absorbent resin in the water-absorbent resin composition is usually not less than 75 weight %, preferably not less than 85 weight %, more preferably not less than 95 weight %, of the water-absorbent resin composition.

The water-absorbent resin composition according to the present invention absorbs not only water, but also various water-containing liquids such as body fluids, physiological saline solution, urine, blood, cement water, and fertilizer-containing water, and is favorably used not only for sanitary materials such as disposable diapers, sanitary napkins and incontinent pads, but also in various industrial fields such as engineering works, agriculture and horticulture, but particularly favorably used for sanitary materials, such as disposable diapers (including infants' toilet training pants with disposable diapers) and incontinent pads, by utilizing the excellent urine resistance of the water-absorbent resin composition wherein the sanitary materials are for the purpose of absorbing urine.

Next, an explanation is made on the absorbent article for which the water-absorbent resin composition according to the present invention is used.

The absorbent article, for which the water-absorbent resin composition according to the present invention is used, comprises: an absorbent layer including the present invention water-absorbent resin composition and a fibrous material; a liquid-permeable surface sheet; and a liquid-impermeable back sheet; wherein the weight ratio, $\alpha$, of the water-absorbent resin composition to the total of the water-absorbent resin composition and the fibrous material is usually not less than 0.2. The weight ratio $\alpha$ is in the range of preferably 0.3 to 1.0, more preferably 0.4 to 0.8.

In the case where the above weight ratio $\alpha$ is less than 0.2, the resultant absorbent article is generally bulky and displays much desorption (wet back). Particularly, the use of the present invention water-absorbent resin composition is very preferable, because this resin composition becomes very little colored in the initial stage and with the passage of time after being produced, and therefore has no problem of coloring even if the water-absorbent resin composition is contained in a high concentration such that $\alpha$ is not less than 0.2. In addition, if the water-absorbent resin composition according to the present invention which satisfies the above-defined offensive-odor reduction ratio is used in a high concentration such that $\alpha$ is not less than 0.2, then the deodorizing effect is very preferably high.

In a production process for this absorbent article, the water-absorbent resin composition is blended or sandwiched with the fibrous material to prepare an absorbent structure (absorbent core), and the resultant absorbent core is sandwiched between a liquid-permeable surface material and a liquid-impermeable base material, and the resultant product is, if necessary, provided with materials such as an elastic member, a diffusion layer, or a pressure sensitive adhesive tape, thus obtaining an absorbent article, particularly, sanitary napkin or diaper for adults. The above absorbent core is subjected to compression forming so as to have a density of 0.06 to 0.5 g/cc and a basis weight of 0.01 to 0.20 g/cm². Incidentally, examples of usable fibrous materials include hydrophilic fibers such as pulverized wood pulp, and other examples include cotton linters, crosslinked cellulose fibers, rayon, cotton, wool, acetate, and vinylon. Preferably, they may be air-laid.

(Effects and Advantages of the Invention)

The water-absorbent resin composition according to the present invention contains an aminoacetic chelating agent, and the total content of the nitrilotriacetic acid (salt) in the water-absorbent resin composition is very low, therefore this water-absorbent resin composition is excellent in the urine resistance and further in the light resistance and becomes little colored and is high safe. In the case where the water-absorbent resin composition further comprises a water-soluble deodorant, the problems which occur when the water-absorbent resin absorbs such as urine can also be solved. The water-absorbent resin composition according to the present invention further exhibits an excellent absorption capacity without load, an excellent eluted deteriorated extractable content, and an excellent absorption capacity under a load.

DETAILED DESCRIPTION OF THE PREFERRED EMBODIMENTS

Hereinafter, the present invention is more specifically illustrated by the following examples of some preferred embodiments in comparison with comparative examples not according to the invention. However, the present invention is not limited thereto.

Unless otherwise noted, the units "part(s)" and "%" and the term "water-absorbent resin (composition)", as hereinafter simply referred to, denote "weight part(s)", "weight %", and "water-absorbent resin or water-absorbent resin composition" respectively.

(1) Absorption capacity of water-absorbent resin (composition) without load:

First, 0.2 g of water-absorbent resin (composition) was uniformly placed into a tea bag type bag (6 cm×6 cm), of which the opening was then sealed by heating, and the bag was then immersed into 0.9% aqueous sodium chloride solution (physiological saline) of room temperature. Sixty minutes later, the bag was drawn up and then drained at 250 G (cm/sec²) for 3 minutes with a centrifuge, and the weight $W_1$ (g) of the bag was then measured. On the other hand, the same procedure was carried out using no water-absorbent resin (composition), and the resultant weight $W_0$ (g) was measured. Thus, the absorption capacity (g/g) without load was calculated from these weights $W_1$ and $W_0$ in accordance with the following equation:

$$\text{absorption capacity (g/g) without load} = (W_1 - W_0)/(\text{weight (g) of water-absorbent resin (composition)}).$$

(2) Extractable content as eluted from water-absorbent resin (composition):

First of all, 1 g of water-absorbent resin (composition) was swollen with 25 ml of artificial urine in a 100 ml beaker, and the beaker was closed and then allowed to stand stationary at 37° C. for 16 hours. Next, the resultant swollen gel was dispersed into 975 ml of deionized water to rinse the eluted extractable components with deionized water. The dispersion was stirred for 1 hour and then filtered off with a paper filter. Next, 50 g of the resultant filtrate was placed into a beaker of 100 ml. Thereto, 1 ml of 0.1 N aqueous sodium hydroxide solution, 10 ml of N/200 aqueous methyl glycol chitosan solution, and 4 drops of 0.1% aqueous Toluidine Blue solution were added, and then the resultant solution in the above beaker was subjected to colloidal titration with an N/400 aqueous poly(potassium vinyl sulfate) solution, when the point at which the color of the solution had changed from blue to reddish violet was regarded as the end point of the titration to determine the titration amount $B_1$ (ml). In addition, the same procedure was carried out without the water-absorbent resin (composition) to determine the titration amount $C_1$ (ml) as the blank. Then, the extractable content (wt %) as eluted from the water-absorbent resin (composition) was calculated from these titration amounts $B_1$ and $C_1$ and the molecular weight $D_1$ of the repeating units of the water-absorbent resin in accordance with the following equation:

$$\text{eluted extractable content (wt \%)} = (C_1 - B_1) \times 0.005 \times D_1.$$

The composition of the artificial urine is as follows:

| | |
|---|---|
| deionized water | 97.1% |
| urea | 1.9% |
| sodium chloride | 0.8% |
| magnesium chloride | 0.1% |
| calcium chloride | 0.1% |

(3) Deteriorated extractable content as eluted from water-absorbent resin (composition):

First of all, 1 g of water-absorbent resin (composition) was swollen to 25 times with artificial urine, containing L-ascorbic acid in a concentration of 0.005 wt %, in a 100 ml plastic container having a cap, and the container was closed and then allowed to stand stationary at 37° C. for 16 hours. Thereafter, the resultant swollen gel was dispersed into 975 g of deionized water to rinse the eluted deteriorated extractable components with deionized water. The dispersion was stirred for 1 hour and then filtered with a paper filter. Next, 50 g of the resultant filtrate was placed into a beaker of 100 ml. Thereto, 1 ml of 0.1 N aqueous sodium hydroxide solution, 10 ml of N/200 aqueous methyl glycol chitosan solution, and 4 drops of 0.1% aqueous Toluidine Blue solution were added, and then the resultant solution in the above beaker was subjected to colloidal titration with an N/400 aqueous poly(potassium vinyl sulfate) solution, when the point at which the color of the solution had changed from blue to reddish violet was regarded as the end point of the titration to determine the titration amount $B_2$ (ml). In addition, the same procedure was carried out without the water-absorbent resin (composition) to determine the titration amount $C_2$ (ml) as the blank. Then, the deteriorated extractable content (wt %) as eluted from the water-absorbent resin (composition) was calculated from these titration amounts $B_2$ and $C_2$ and the molecular weight $D_2$ of the repeating units of the water-absorbent resin in accordance with the following equation:

$$\text{eluted deteriorated extractable content (wt \%)} = (C_2 - B_2) \times 0.005 \times D_2.$$

(4) Absorption capacity under load:

The absorption capacity under a load was determined using a measurement apparatus of FIG. 1. As is shown in FIG. 1, the measurement apparatus comprises: a balance 1; a container 2 of a predetermined capacity as mounted on the balance 1; an air-intake pipe 3; a conduit 4; a glass filter 6; and a measurement section 5 as mounted on the glass filter 6. The container 2 has an opening 2a on the top and an opening 2b on the side. The air-intake pipe 3 is inserted through the opening 2a, and the conduit 4 is fitted to the opening 2b. In addition, the container 2 is filled with a predetermined amount of 0.9% aqueous sodium chloride solution (hereinafter referred to as physiological saline solution) 12. The lower part of the air-intake pipe 3 is submerged in the physiological saline solution 12. The air-intake pipe 3 is set to keep the internal pressure of the container 2 substantially atmospheric pressure. The glass filter 6 is formed in a diameter of 55 mm. The container 2 and the glass filter 6 are connected to each other through the conduit 4 made of silicone resin. In addition, the position and level of the glass filter 6 are fixed relative to the container 2. The measurement section 5 comprises: a paper filter 7; a supporting cylinder 9; a metal gauze 10 as attached to the bottom of the supporting cylinder 9; and a weight 11. The measurement section 5 is formed by mounting the paper filter 7 and the supporting cylinder 9 (i.e. metal gauze 10) in this order on the glass filter 6. The metal gauze 10 is made of stainless steel and has a mesh opening size of 400 mesh (38 μm). The level of the upper face of the metal gauze 10, in other words, the level of the contact face of the metal gauze 10 with a water-absorbent resin (composition) 15, is set so as to be as high as the level of the lower end face 3a of the air-intake pipe 3. On the metal gauze 10, a predetermined amount of water-absorbent resin (composition) 15 is uniformly spread. The weight 11 is adjusted in weight such that a load of 4.83 kPa or 1.9 kPa can uniformly be applied to the metal gauze 10, in other words, to the water-absorbent resin (composition) 15.

The absorption capacity under a load was measured with the measurement apparatus having the above-mentioned constitution. The measurement method is hereinafter explained.

First, predetermined preparatory operations were made, in which, for example, a predetermined amount of physiological saline solution 12 was placed into the container 2, and the air-intake pipe 3 was inserted into the container 2. Next, the paper filter 7 was mounted on the glass filter 6. On the other hand, in parallel with these mounting operations, 0.9 g of water-absorbent resin (composition) 15 was uniformly spread inside the supporting cylinder 9, in other words, on the metal gauze 10, and the weight 11 was put on this water-absorbent resin (composition) 15. Next, the metal gauze 10, in other words, the supporting cylinder 9 (in which the water-absorbent resin (composition) 15 and the weight 11 were put), was mounted on the paper filter 7 such that the center line of the supporting cylinder 9 would conform with that of the glass filter 6. Then, the weight of the physiological saline solution, as absorbed by the water-absorbent resin (composition) 15 over a period of 60 minutes since the supporting cylinder 9 had been mounted on the paper filter 7, was determined from a value as measured with the balance 1. In addition, the same procedure as the above was carried out using no water-absorbent resin (composition) 15, and the weight of the physiological saline solution, as absorbed by materials other than the water-absorbent resin (composition) 15, was determined from a value as measured with the balance 1 to regard this determined weight as the blank value. The absorption capacity under a load was calculated from the following equation:

absorption capacity (g/g) under load=(water absorption quantity in 60 minutes−blank value)/(weight (g) of water-absorbent resin (composition)).

(5) Analysis of chelating agent:

The chelating agent was dissolved into water to analyze the total content of the nitrilotriacetic acid (salt) in the chelating agent by high performance liquid chromatography under the following conditions:

(eluents): 0.3 ml of 0.4 mol/L alum solution, 450 ml of 0.1N-KOH solution, 3 ml of 40% aqueous tetra-n-butylammonium hydroxide solution, 3 ml of sulfuric acid, 2,550 ml of water, 1.5 ml of ethylene glycol (column):LichroCART 250-4 Superspher 100 RP-18e (4 μm) produced by Merk (flow rate): 1 ml/minute (detector): UV 258 nm (injection): 50 μl (6) Total content of nitrilotriacetic acid (salt) in water-absorbent resin composition:

An amount of 1 g of water-absorbent resin composition was stirred in 100 g of physiological saline solution for 1 hour and then filtered off to measure the total content of the nitrilotriacetic acid (salt) in the resultant filtrate by the liquid chromatography of (5) above, thereby quantifying the total content of the nitrilotriacetic acid (salt) in the water-absorbent resin composition.

(7) Evaluation method for coloring of water-absorbent resin composition with passage of time:

First, 2.000 g of water-absorbent resin composition (unless otherwise noted, dry powder of 600 to 300 μm in particle diameter) was spread onto the bottom of a polypropylene vessel (capacity 120 cc, Pack-Ace made by Teraoka Co., Ltd.) of 55 mm in inner diameter and 70 mm in height, and then left stationary at 70° C. under 80% RH atmosphere for 5 days in a thermo-humidistat (PLATINOUS LUCIFER, model No. PL-2G, made by Tabai Especk Co., Ltd.) in the open system with no cap on the vessel. Incidentally, the amount of the above water-absorbent resin composition as spread per unit area (0.084 g/cm$^2$) is a model amount in the high concentration core.

After 5 days, the entirety of the water-absorbent resin composition in the vessel was filled into the below-mentioned powder-paste sample stand (30 mm φ), and the surface color of the water-absorbent resin composition was measured in terms of the yellowness index (YI) under set conditions (reflection measurement/appendix powder-paste sample stand (30 mm φ)/standard round white board No. 2/30 mm φ projector pipe for powder-paste as the standard) using a spectroscopic color difference meter (SZ-Σ80 COLOR MEASURING SYSTEM, made by Nippon Denshoku Kogyo Co., Ltd.).

(8) Measurement of deodorizability (evaluation method for offensive-odor reduction ratio):

First, 5 g of water-absorbent resin composition was placed into an airtight polypropylene vessel (250 cc, Pack-Ace, made by Teraoka Co., Ltd.) of 69 mm in opening diameter, 63 mm in bottom diameter, 97 mm in height, and 250 ml in capacity. Next, the vessel was further charged with 30 g of artificial urine to which 0.5 ml of an aqueous solution as prepared by diluting a 15% aqueous sodium methylmercaptan solution (made by Tokyo Kasei Kogyo Co., Ltd.) as an offensively odorous component to 500 times with deionized water had been added, and then the vessel was capped and sealed for gases not to leak therefrom. The vessel was left stationary under conditions of 25° C., 55% RH for 4 hours, and then the concentration of methylmercaptan in the space in the vessel was measured with a detector and a detecting tube of Gas Tech Co., Ltd. to refer to the obtained result as G1. The detecting tube as used was No. 70 of Gas Tech Co., Ltd. for all mercaptans (measurement range: 0.5 to 120 ppm). The measurement method was carried out by operation as prescribed for the detecting tube as follows. The detecting tube was used in a way of one-time suction (100 ml, 2 minutes). In the case where the concentration of not more than 5 ppm was measured, the suction was carried out 2 to 10 times, and the read value was divided by the number of the times of the suction. The detecting tube as used was corrected with ethylmercaptan, therefore the concentration was measured by multiplying methylmercaptan by a calculation factor of 0.7 (number of times of suction=1).

Next, the concentration of methylmercaptan in the space in the vessel was measured in the same way as the above except that the vessel was charged not with the water-absorbent resin composition and the artificial urine, but with 0.5 ml of the aqueous solution as prepared by diluting the 15% aqueous sodium methylmercaptan solution (made by Tokyo Kasei Kogyo Co., Ltd.) to 500 times with deionized water, and the obtained result was referred to as G0.

Then, the offensive-odor reduction ratio was calculated from the following equation:

offensive-odor reduction ratio (%)=(G0−G1)/G0×100.

REFERENTIAL EXAMPLE 1

An aqueous monomer solution was prepared by mixing 67.0 parts of a 37% aqueous sodium acrylate solution, 10.2 parts of acrylic acid, 0.079 parts of polyethylene glycol diacrylate (average number of ethylene oxide units: 8), and 22.0 parts of water together. Nitrogen was blown into the above aqueous monomer solution in a vat, thus reducing the concentration of dissolved oxygen in the solution to not higher than 0.1 ppm.

Then, the temperature of the above aqueous monomer solution was adjusted to 18° C. under nitrogen atmosphere. Next, thereto 0.16 parts of a 5% aqueous sodium persulfate solution, 0.16 parts of a 5% aqueous 2,2'-azobis(2-amidinopropane) dihydrochloride solution, 0.15 parts of a 0.5% aqueous L-ascorbic acid solution, and 0.17 parts of a 0.35% aqueous hydrogen peroxide solution were dropwise added in sequence under stirred conditions.

Immediately after the dropwise addition of hydrogen peroxide, a polymerization reaction started. Then, stirring was stopped and, after 10 minutes, the temperature of the monomers reached the peak temperature. The peak temperature was 85° C. Then, the vat was immersed into a hot water bath of 80° C. and aged for 10 minutes.

The resultant transparent hydrogel was crushed with a meat chopper and then dried at 180° C. for 30 minutes.

The resultant dry product was pulverized with a pulverizing machine and then classified into what passed through a screen of 500 μm, but remained on a screen of 105 μm, thus obtaining a water-absorbent resin (A).

A composition solution, comprising 0.05 parts of ethylene glycol diglycidyl ether, 1 part of propylene glycol, 3 parts of water, and 1 part of isopropyl alcohol, was mixed with 100 parts of the water-absorbent resin (A), and the resultant mixture was treated by heating at 180° C. for 40 minutes, thus obtaining a surface-treated water-absorbent resin (B).

The physical property measurement results of this surface-treated water-absorbent resin (B) are shown in Table 1.

EXAMPLE 1

Sixty percent sulfuric acid was added to a commercially available aqueous pentasodium diethylenetriaminepentaacetate solution (solid content: 40%) under stirred conditions to adjust pH into the range of 1.8 to 2. The resultant solution was left stationary for a while, and then the deposited diethylenetriaminepentaacetic acid was filtered off and then washed with pure water and then dried at 60° C.

The total content of the nitrilotriacetic acid (salt) in the above commercially available pentasodium diethylenetriaminepentaacetate was about 5%, but the total content of the nitrilotriacetic acid (salt) in the resultant diethylenetriaminepentaacetic acid was reduced to 35 ppm of the diethylenetriaminepentaacetic acid by the above treatment.

A treating agent solution, as prepared by adding 0.05 parts of ethylene glycol diglycidyl ether, 1 part of propylene glycol, 3 parts of water, and 1 part of isopropyl alcohol to 0.002 parts of the above-obtained diethylenetriaminepentaacetic acid having the reduced total content of the nitrilotriacetic acid (salt), was mixed with 100 parts of the water-absorbent resin (A) (as obtained in Referential Example 1), and the resultant mixture was treated by heating at 180° C. for 40 minutes, thus obtaining a water-absorbent resin composition (1) (in which the mixing ratio of the diethylenetriaminepentaacetic acid was 20 ppm of the water-absorbent resin (A)).

The total content of the nitrilotriacetic acid (salt) in the water-absorbent resin composition (1) was measured. As a result, it was 0.1 ppm or less of this composition, therefore, unmeasurable. The physical property measurement results of the water-absorbent resin composition (1) are shown in Table 1.

EXAMPLE 2

A water-absorbent resin composition (2) was obtained in the same way as of Example 1 except that the amount of diethylenetriaminepentaacetic acid in the treating agent solution was changed to 0.01 part (the mixing ratio of the diethylenetriaminepentaacetic acid in the resultant composition was 100 ppm of the water-absorbent resin (A)).

The total content of the nitrilotriacetic acid (salt) in the water-absorbent resin composition (2) was measured. As a result, it was 0.1 ppm or less of this composition, therefore, unmeasurable. The physical property measurement results of the water-absorbent resin composition (2) are shown in Table 1.

EXAMPLE 3

A 0.07% aqueous solution was prepared by dissolving into water the diethylenetriaminepentaacetic acid (as obtained in Example 1) having the reduced total content of the nitrilotriacetic acid (salt). An amount of 3 parts of this solution was sprayed to 100 parts of the water-absorbent resin (B) (as obtained in Referential Example 1) and then dried at 80° C., thus obtaining a water-absorbent resin composition (3) (in which the mixing ratio of the diethylenetriaminepentaacetic acid was 21 ppm of the water-absorbent resin (B)).

The total content of the nitrilotriacetic acid (salt) in the water-absorbent resin composition (3) was measured. As a result, it was 0.1 ppm or less of this composition, therefore, unmeasurable. The physical property measurement results of the water-absorbent resin composition (3) are shown in Table 1.

EXAMPLE 4

A water-absorbent resin composition (4) was obtained in the same way as of Example 3 except that the concentration of the aqueous diethylenetriaminepentaacetic acid solution was changed to 0.5% (the mixing ratio of the diethylenetriaminepentaacetic acid in the resultant composition was 150 ppm of the water-absorbent resin (B)).

The total content of the nitrilotriacetic acid (salt) in the water-absorbent resin composition (4) was measured. As a result, it was 0.1 ppm or less of this composition, therefore, unmeasurable. The physical property measurement results of the water-absorbent resin composition (4) are shown in Table 1.

EXAMPLE 5

A 0.1% aqueous solution was prepared by dissolving into water the diethylenetriaminepentaacetic acid (as obtained in Example 1) having the reduced total content of the nitrilotriacetic acid (salt).

A water-absorbent resin composition (5) was obtained by carrying out the steps of drying, pulverization, and surface treatment in the same way as of Referential Example 1 except that 3.5 parts of the above aqueous solution was added when 100 parts of the gel resultant from the polymerization was crushed with the meat chopper (the mixing ratio of the diethylenetriaminepentaacetic acid in the resultant composition was 100 ppm of the solid content (substantially, water-absorbent resin) in the gel).

The total content of the nitrilotriacetic acid (salt) in the water-absorbent resin composition (5) was measured. As a result, it was 0.1 ppm or less of this composition, therefore, unmeasurable. The physical property measurement results of the water-absorbent resin composition (5) are shown in Table 1.

EXAMPLE 6

A 35% aqueous tetrasodium diethylenetriaminepentaacetate solution was prepared by mixing together sodium hydroxide, water and the diethylenetriaminepentaacetic acid (as obtained in Example 1) having the reduced total content of the nitrilotriacetic acid (salt). This aqueous solution was diluted to 200 times with water.

An amount of 3 parts of this diluted solution was sprayed to 100 parts of the water-absorbent resin (B) (as obtained in Referential Example 1) to make a mixture, which was then heated at 80° C., thus obtaining a water-absorbent resin composition (6) (in which the mixing ratio of the tetrasodium diethylenetriaminepentaacetate was 52.5 ppm of the water-absorbent resin (B)).

The total content of the nitrilotriacetic acid (salt) in the water-absorbent resin composition (6) was measured. As a result, it was 0.1 ppm or less of this composition, therefore, unmeasurable. The physical property measurement results of the water-absorbent resin composition (6) are shown in Table 1.

EXAMPLE 7

A treating agent solution, comprising 3 parts of the diluted solution (as obtained in Example 6), 0.05 parts of ethylene glycol diglycidyl ether, 1 part of propylene glycol, and 1 part of isopropyl alcohol, was mixed with 100 parts of the water-absorbent resin (A) (as obtained in Referential Example 1), and the resultant mixture was treated by heating at 180° C. for 40 minutes, thus obtaining a water-absorbent resin composition (7) (in which the mixing ratio of the tetrasodium diethylenetriaminepentaacetate was 52.5 ppm of the water-absorbent resin (A)).

The total content of the nitrilotriacetic acid (salt) in the water-absorbent resin composition (7) was measured. As a result, it was 0.1 ppm or less of this composition, therefore, unmeasurable. The physical property measurement results of the water-absorbent resin composition (7) are shown in Table 1.

EXAMPLE 8

Sixty percent sulfuric acid was added to a commercially available aqueous hexasodium triethylenetetraminehexaacetate solution (solid content: 40%) under stirred conditions to adjust pH into the range of 1.8 to 2. The resultant solution was left stationary for a while, and then the deposited triethylenetetraminehexaacetic acid was filtered off and then washed with pure water and then dried at 60° C.

The total content of the nitrilotriacetic acid (salt) in the resultant triethylenetetraminehexaacetic acid was 20 ppm of the triethylenetetraminehexaacetic acid.

A 35% aqueous pentasodium triethylenetetraminehexaacetate solution was prepared by mixing together sodium hydroxide, water and the above-obtained triethylenetetraminehexaacetic acid having the reduced total content of the nitrilotriacetic acid (salt). This aqueous solution was diluted to 200 times with water.

An amount of 3 parts of this diluted solution was sprayed to 100 parts of the water-absorbent resin (B) (as obtained in Referential Example 1) to make a mixture, which was then heated at 80° C., thus obtaining a water-absorbent resin composition (8) (in which the mixing ratio of the pentasodium triethylenetetraminehexaacetate was 52.5 ppm of the water-absorbent resin (B)).

The total content of the nitrilotriacetic acid (salt) in the water-absorbent resin composition (8) was measured. As a result, it was 0.1 ppm or less of this composition, therefore, unmeasurable. The physical property measurement results of the water-absorbent resin composition (8) are shown in Table 1.

COMPARATIVE EXAMPLE 1

A comparative water-absorbent resin composition (1) was obtained in the same way as of Example 2 except that the diethylenetriaminepentaacetic acid having the reduced total content of the nitrilotriacetic acid (salt) was replaced with an aqueous solution as prepared by dissolving the commercially available pentasodium diethylenetriaminepentaacetate, as it was, into water.

The total content of the nitrilotriacetic acid (salt) in the comparative water-absorbent resin composition (1) was 5 ppm of this composition.

The physical property measurement results of the comparative water-absorbent resin composition (1) are shown in Table 1.

REFERENTIAL EXAMPLE 2

An aqueous monomer solution was prepared by mixing 76 parts of a 37% aqueous sodium acrylate solution, 7 parts of acrylic acid, 0.05 parts of polyethylene glycol diacrylate (average number of ethylene oxide units: 8) and 15 parts of water together.

Nitrogen was blown into the above aqueous monomer solution in a jacketed twin-arm kneader, thus removing dissolved oxygen from the solution. Then, the temperature of the aqueous monomer solution was adjusted to 22° C.

Next, 1 part of a 5% aqueous sodium persulfate solution and 0.04 parts of a 0.5% aqueous L-ascorbic acid solution were added under stirred conditions. One minute later than this addition, the aqueous monomer solution began clouding and its temperature began rising. After another 20 minutes, the temperature reached the peak temperature, and the solution was then aged for 20 minutes under stirred conditions. The peak temperature was 94° C.

After the aging had finished, the resultant gel was got out and then dried at 170° C. for 65 minutes. The resultant dry polymer was pulverized and then classified into what passed through a screen of 850 μm, but remained on a screen of 105 μm, thus obtaining a water-absorbent resin (C).

A composition solution, comprising 0.05 parts of ethylene glycol diglycidyl ether, 1 part of propylene glycol, 3 parts of water, and 1 part of isopropyl alcohol, was mixed with 100 parts of the water-absorbent resin (C), and the resultant mixture was treated by heating at 180° C. for 40 minutes, thus obtaining a surface-treated water-absorbent resin (D).

The physical property measurement results of this surface-treated water-absorbent resin (D) are shown in Table 1.

EXAMPLE 9

A 35% aqueous tetrasodium diethylenetriaminepentaacetate solution was prepared by mixing together sodium hydroxide, deionized water and the diethylenetriaminepentaacetic acid (as obtained in Example 1) having the reduced total content of the nitrilotriacetic acid (salt).

This aqueous solution was diluted to 200 times with deionized water, and then 3 parts of the diluted solution was sprayed to 100 parts of the water-absorbent resin (D) (as obtained in Referential Example 2) to make a mixture, which was then heated at 80° C., thus obtaining a water-absorbent resin composition (9) (in which the mixing ratio of the tetrasodium diethylenetriaminepentaacetate was 52.5 ppm of the water-absorbent resin (D)).

The total content of the nitrilotriacetic acid (salt) in the water-absorbent resin composition (9) was measured. As a result, it was 0.1 ppm or less of this composition, therefore, unmeasurable. The physical property measurement results of the water-absorbent resin composition (9) are shown in Table 1.

COMPARATIVE EXAMPLE 2

The commercially available aqueous pentasodium diethylenetriaminepentaacetate solution as used in Example 1 was diluted to 200 times with deionized water. An amount of 3 parts of this diluted solution was sprayed to 100 parts of the water-absorbent resin (D) (as obtained in Referential Example 2) to make a mixture, which was then heated at 80° C., thus obtaining a comparative water-absorbent resin composition (2).

The total content of the nitrilotriacetic acid (salt) in the comparative water-absorbent resin composition (2) was 3 ppm of this composition. The physical property measurement results of the comparative water-absorbent resin composition (2) are shown in Table 1.

(Comparison of Light Resistance)

An amount of 1 g each of the water-absorbent resin composition (9), the comparative water-absorbent resin composition (2), and the water-absorbent resin (D) (as obtained in Example 9, Comparative Example 2, and Referential Example 2 respectively) was swollen with 100 g of deionized water in a polypropylene container, which was then capped and then left stationary inside a sunny window for 5 days.

After being left stationary for 5 days in the above way, the resultant gel was dispersed into 900 ml of deionized water to rinse the eluted extractable components with deionized water. The dispersion was stirred for 1 hour and then filtered with a paper filter. The resultant filtrate was titrated by colloid titration to determine the extractable content (%) as eluted from each water-absorbent resin (composition). The lower this extractable content (%) is, the higher the light resistance is. The results are as follows:

| | |
|---|---|
| water-absorbent resin composition (9) | 32% |
| comparative water-absorbent resin composition (2) | 50% |
| water-absorbent resin (D) | 50% |

From the above results, it is found that an aminoacetic chelating agent containing a large amount of nitrilotriacetic acid (salt) cannot enhance the light resistance, but that the reduction of the total content of the nitrilotriacetic acid (salt) can enhance the light resistance.

EXAMPLE 10

A 40% aqueous pentasodium diethylenetriaminepentaacetate solution was prepared by mixing together sodium hydroxide, deionized water and the diethylenetriaminepentaacetic acid (as obtained in Example 1) having the reduced total content of the nitrilotriacetic acid (salt).

Sixty percent sulfuric acid was added to the resultant aqueous pentasodium diethylenetriaminepentaacetate solution (solid content: 40 %) under stirred conditions to adjust pH into the range of 1.8 to 2. The resultant solution was left stationary for a while, and then the deposited diethylenetriaminepentaacetic acid was filtered off and then washed with pure water and then dried at 60° C.

The total content of the nitrilotriacetic acid (salt) in the resultant diethylenetriaminepentaacetic acid was 0.1 ppm or less of this diethylenetriaminepentaacetic acid, therefore, unmeasurable.

A 35% aqueous tetrasodium diethylenetriaminepentaacetate solution was prepared by mixing together sodium hydroxide, deionized water and the above-obtained diethylenetriaminepentaacetic acid having the reduced total content of the nitrilotriacetic acid (salt). This aqueous solution was diluted to 200 times with deionized water.

An amount of 3 parts of this diluted solution was sprayed to 100 parts of the water-absorbent resin (B) (as obtained in Referential Example 1) to make a mixture, which was then heated at 80° C., thus obtaining a water-absorbent resin composition (10) (in which the mixing ratio of the tetrasodium diethylenetriaminepentaacetate was 52.5 ppm of the water-absorbent resin (B)).

The total content of the nitrilotriacetic acid (salt) in the water-absorbent resin composition (10) was measured. As a result, it was 0.1 ppm or less of this composition, therefore, unmeasurable. The physical property measurement results of the water-absorbent resin composition (10) are shown in Table 1.

EXAMPLE 11

A water-absorbent resin composition (11) was obtained in the same way as of Example 10 except that the water-absorbent resin (B) (as obtained in Referential Example 1) was replaced with the water-absorbent resin (D) (as obtained in Referential Example 2) (the mixing ratio of the tetrasodium diethylenetriaminepentaacetate in the resultant composition was 52.5 ppm of the water-absorbent resin (D)).

The total content of the nitrilotriacetic acid (salt) in the water-absorbent resin composition (11) was measured. As a result, it was 0.1 ppm or less of this composition, therefore, unmeasurable. The physical property measurement results of the water-absorbent resin composition (11) are shown in Table 1.

EXAMPLE 12

A water-absorbent resin composition (12) was obtained by the same production process as that for the water-absorbent resin composition (10) in Example 10 except that: an aqueous solution was prepared such that a commercially available water-soluble deodorant (15% aqueous solution of extractates from leaves of Theaceae plants) would be present in a concentration of 16.7% in an aqueous solution as diluted to 200 times; 3 parts of the resultant aqueous solution was sprayed to 100 parts of the water-absorbent resin (B) (as obtained in Referential Example 1) to make a mixture, which was then heated at 80° C; and an inorganic powder comprising silicon dioxide (Aerosil 200 made by Nippon Aerosil Co., Ltd.) was then added to the heated mixture in the ratio of 0.5%.

EXAMPLE 13

A water-absorbent resin composition (13) was obtained by the same production process as that for the water-absorbent resin composition (11) in Example 11 except that: an aqueous solution was prepared such that a commercially available water-soluble deodorant (15% aqueous solution of extractates from leaves of Theaceae plants) would be present in a concentration of 16.7% in an aqueous solution as diluted to 200 times; and 3 parts of the resultant aqueous solution was mixed with 100 parts of the water-absorbent resin (D) (as obtained in Referential Example 2) by stirring.

EXAMPLE 14

A water-absorbent resin composition (14) was obtained by the same production process as that for the water-absorbent resin composition (10) in Example 10 except that: an aqueous solution was prepared such that a commercially available water-soluble deodorant (Oaklean EX made by TAIYO KORYO Co., Ltd.) would be present in a concentration of 16.7% in an aqueous solution as diluted to 200 times; and 3 parts of the resultant aqueous solution was sprayed to 100 parts of the water-absorbent resin (B) (as obtained in Referential Example 1) to mix them together.

EXAMPLE 15

A water-absorbent resin composition (15) was obtained by adding a commercially available water-soluble deodorant (Eporion made by Aiko Co., Ltd.) to 100 parts of the water-absorbent resin composition (10) (as obtained in Example 10) in the ratio of 0.5% to mix them together.

TABLE 1

| Water-absorbent resin (composition) | Absorption capacity (g/g) without load | Extractable content (%) as eluted | Deteriorated extractable content (%) as eluted | Absorption capacity (g/g) under load of 4.83 kPa | Absorption capacity (g/g) under load of 1.9 kPa | Light resistance (%) | Yellowness index (YI) Before test | Yellowness index (YI) After test (after 5 days) | Deodorizing effect (offensive-odor reduction ratio (%)) |
|---|---|---|---|---|---|---|---|---|---|
| (B) | 34 | 11 | 25 | 27 | 33 | — | — | — | — |
| (1) | 34 | 11 | 14 | 29 | 33 | — | 12.6 | 19.8 | — |
| (2) | 34 | 11 | 12 | 28 | 33 | — | — | — | — |
| (3) | 34 | 11 | 15 | 27 | 33 | — | — | — | — |
| (4) | 34 | 11 | 11 | 27 | 33 | — | — | — | — |
| (5) | 34 | 11 | 12 | 27 | 33 | — | — | — | — |
| (6) | 34 | 11 | 14 | 27 | 33 | — | — | — | — |
| (7) | 34 | 11 | 12 | 29 | 33 | — | — | — | — |

TABLE 1-continued

| Water-absorbent resin (composition) | Absorption capacity (g/g) without load | Extractable content (%) as eluted | Deteriorated extractable content (%) as eluted | Absorption capacity (g/g) under load of 4.83 kPa | Absorption capacity (g/g) under load of 1.9 kPa | Light resistance (%) | Yellowness index (YI) Before test | Yellowness index (YI) After test (after 5 days) | Deodorizing effect (offensive-odor reduction ratio (%)) |
|---|---|---|---|---|---|---|---|---|---|
| (8) | 34 | 11 | 12 | 27 | 33 | — | — | — | — |
| Comparative (1) | 34 | 11 | 12 | 28 | 33 | — | 13.1 | 36.8 | — |
| (D) | 46 | 16 | 35 | 24 | 38 | 50 | — | — | — |
| (9) | 45 | 16 | 18 | 24 | 38 | 32 | 14.1 | 23.4 | — |
| Comparative (2) | 45 | 16 | 19 | 24 | 38 | 50 | 13.4 | 32.7 | — |
| (10) | 34 | 11 | 12 | 27 | 33 | — | — | — | 28 |
| (11) | 45 | 16 | 18 | 24 | 38 | — | — | — | — |
| (12) | 34 | 11 | 12 | — | 28 | — | — | — | 45 |
| (13) | 45 | 16 | 18 | — | 38 | — | — | — | 53 |
| (14) | 34 | 11 | 12 | — | 33 | — | — | — | 41 |
| (15) | 34 | 11 | 12 | — | 33 | — | — | — | 30 |

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A particulate water-absorbent resin composition, which comprises a water-absorbent resin and an aminoacetic chelating agent, wherein the mixing ratio of the aminoacetic chelating agent in the water-absorbent resin composition is not less than 10 ppm of the water-absorbent resin, and wherein the total content of nitrilotriacetic acid and its salt in the water-absorbent resin composition is not more than 1 ppm of the water-absorbent resin composition and where the ratio of said water absorbent resin based on the weight of said particulate water-absorbent composition is not less than 75 weight %.

2. A water-absorbent resin composition, which comprises a water-absorbent resin and an aminoacetic chelating agent, wherein the total content of nitrilotriacetic acid and its salt relative to the aminoacetic chelating agent in the water-absorbent resin composition is not more than 1,000 ppm.

3. A water-absorbent resin composition according to claim 1, which further comprises a water-soluble deodorant.

4. A water-absorbent resin composition according to claim 2, which further comprises a water-soluble deodorant.

5. A water-absorbent resin composition according to claim 1, which exhibits an absorption capacity of not less than 30 g/g without load, an eluted deteriorated extractable content of not more than 20 weight %, an absorption capacity of not less than 28 g/g under a load of 1.9 kPa, and a yellowness index of not more than 26.

6. A water-absorbent resin composition according to claim 2, which exhibits an absorption capacity of not less than 30 g/g without load, an eluted deteriorated extractable content of not more than 20 weight %, an absorption capacity of not less than 28 g/g under a load of 1.9 kPa, and a yellowness index of not more than 26.

7. A water-absorbent resin composition according to claim 3, which exhibits an absorption capacity of not less than 30 g/g without load, an eluted deteriorated extractable content of not more than 20 weight %, an absorption capacity of not less than 28 g/g under a load of 1.9 kPa, and a yellowness index of not more than 26.

8. A water-absorbent resin composition according to claim 4, which exhibits an absorption capacity of not less than 30 g/g without load, an eluted deteriorated extractable content of not more than 20 weight %, an absorption capacity of not less than 28 g/g under a load of 1.9 kPa, and a yellowness index of not more than 26.

9. A particulate water-absorbent resin composition, which comprises a water-absorbent resin and a water-soluble deodorant and exhibits an absorption capacity of not less than 30 g/g without load, an eluted deteriorated extractable content of not more than 20 weight %, an absorption capacity of not less than 28 g/g under a load of 1.9 kPa, and an offensive-odor reduction ratio of not less than 40%, where the ratio of said water absorbent resin based on the weight of said particulate water-absorbent composition is not less than 75 weight %.

10. The particulate water-absorbent resin composition of claim 1, wherein said water-absorbent resin is a partially-neutralized and crosslinked poly(acrylic acid) obtained by a process of polymerizing a hydrophilic monomer including a major portion of a monomer component selected from the group consisting of acrylic acid, acrylic acid salts, and mixtures thereof.

11. The particulate water-absorbent resin composition of claim 9, wherein said water-absorbent resin is a partially-neutralized and crosslinked poly(acrylic acid) obtained by a process of polymerizing a hydrophilic monomer including a major portion of a monomer component selected from the group consisting of acrylic acid, acrylic acid salts, and mixtures thereof.

12. A sanitary material, comprising the water-absorbent resin composition of claim 1.

13. A sanitary material, comprising the water-absorbent resin composition of claim 9.

14. The water-absorbent resin composition of claim 1, wherein said aminoacetic chelating agent is prepared by a process of adjusting an aqueous solution of said aminoacetic chelating agent to a pH of 1 to 3, precipitating said aminoacetic chelating agent from said solution to form a precipitate, and recovering said precipitate of said aminoacetic chelating agent.

15. The water-absorbent resin composition of claim 14, wherein said precipitate of said aminoacetic chelating agent contains not more than 1,000 ppm nitrilotriacetic acid or salts thereof based on said aminoacetic chelating agent.

16. The particulate water-absorbent resin of claim 9, further comprising an aminoacetic chelating agent.

17. The particulate water-absorbent resin composition of claim 16, wherein said aminoacetic chelating agent is prepared by a process of adjusting an aqueous solution of said aminoacetic chelating agent to a pH of 1 to 3, precipitating said aminoacetic chelating agent from said solution to form a precipitate, and recovering said precipitate of said aminoacetic chelating agent.

18. The particulate water-absorbent resin composition of claim 1, wherein said aminoacetic chelating agent is mixed with said water-absorbent resin by the addition step of said aminoacetic chelating agent, where said addition step is one or more steps selected from the group consisting of (1) the addition to a monomer,
(2) the addition to the resulting gel during polymerization or after polymerization of a monomer,
(3) the addition during surface-crosslinking treatment of said water-absorbent resin,
(4) the addition after surface-crosslinking treatment of said water-absorbent resin, and
(5) the addition in the recovery step of recovering fine particles of the water-absorbent resin.

19. An aminoacetic chelating agent for a particle water-absorbent resin composition of claim 1, wherein said aminoacetic chelating agent contains not more than 1,000 ppm nitrilotriacetic acid or salts thereof based on the aminoacetic chelating agent.

* * * * *